United States Patent [19]

Detty

[11] Patent Number: 5,472,414
[45] Date of Patent: Dec. 5, 1995

[54] UNIVERSAL FIT ANKLE BRACE

[75] Inventor: Michael K. Detty, Tucson, Ariz.

[73] Assignee: Pro Orthopedic Devices, Inc., Tucson, Ariz.

[21] Appl. No.: 319,854

[22] Filed: Oct. 7, 1994

[51] Int. Cl.⁶ ........................................ A61F 5/00
[52] U.S. Cl. .................. 602/27; 128/871; 128/882; 602/23; 602/60; 602/65
[58] Field of Search .................. 602/5, 23, 27, 602/61, 65, 77, 60; 128/871, 882

[56] References Cited

U.S. PATENT DOCUMENTS

| | | | |
|---|---|---|---|
| 3,298,365 | 1/1967 | Lewis | 602/27 |
| 3,506,000 | 4/1970 | Baker. | |
| 3,970,083 | 7/1976 | Carrigan. | |
| 4,313,433 | 2/1982 | Cramer | 602/27 |
| 4,323,058 | 4/1982 | Detty. | |
| 4,495,942 | 1/1985 | Palumbo | 602/27 |
| 4,587,962 | 5/1986 | Greene et al.. | |
| 4,597,395 | 7/1986 | Barlow et al.. | |
| 4,624,244 | 11/1986 | Taheri. | |
| 4,727,863 | 3/1988 | Nelson. | |
| 4,729,370 | 3/1988 | Kallassy | 602/27 |
| 4,926,846 | 5/1990 | Nassar. | |
| 4,974,343 | 12/1990 | Davidson | 36/89 |
| 5,139,479 | 8/1992 | Peters | 602/27 |
| 5,242,379 | 9/1993 | Harris et al. | 602/27 |
| 5,366,439 | 11/1994 | Peters | 602/27 |
| 5,393,303 | 2/1995 | Shiono | 602/27 |

FOREIGN PATENT DOCUMENTS 2241170  8/1991  United Kingdom ............. 602/27

Primary Examiner—Richard J. Apley
Assistant Examiner—Kim M. Lee
Attorney, Agent, or Firm—Caesar, Rivise, Bernstein, Cohen & Pokotilow, Ltd. Caesar

[57] ABSTRACT

A one-size-fits-all ankle brace has a base member which is a unitary piece of elastomeric material, e.g., plush fabric covered neoprene, having an upper portion including a pair of mounting straps, and a lower portion including a pair of mounting straps and a pair of short elastic tension straps attached to the lower portion adjacent respective lower mounting straps. The base member can be folded to form a jacket, wherein the upper mounting straps of the base member are wrapped around the ankle and the leg just above the ankle and the lower mounting straps of the base member wrapped around the ankle, arch, and instep. VELCRO® fastening components hold the mounting straps in place to secure the brace on the ankle. The upper mounting straps overlap each other from opposite directions than the lower mounting straps. The tension straps are criss-crossed across the jacket and are releasably secured to the upper mounting straps by VELCRO® fastening components. The amount that the tension straps are stretched effects the adjustment of the tension they provide for to the brace to stabilize the ankle. The material of the brace provides cushioning and thermal retention properties, thereby protecting the ankle from impact and helping to maintain the ankle at elevated temperatures to prevent injury and facilitate healing.

19 Claims, 3 Drawing Sheets

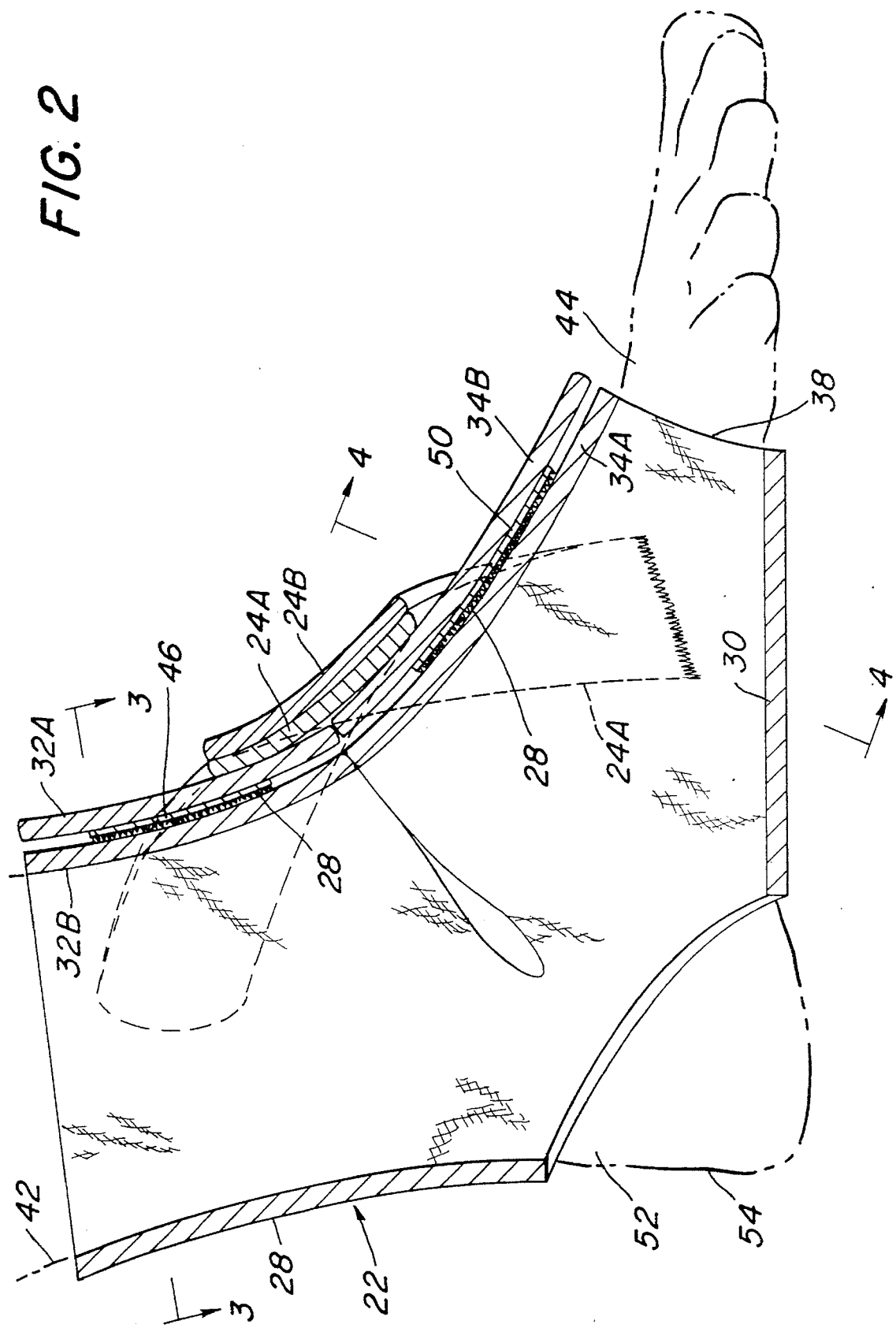

UNIVERSAL FIT ANKLE BRACE

BACKGROUND OF THE INVENTION

This invention relates generally to ankle braces and in particular to ankle braces which are of the "one-size-fits-all" type, that is, they can fit a large range of ankle sizes.

Persons engaged in athletic activities involving walking, running and/or jumping, frequently utilize some support means on their ankle(s) in order to protect the ankle(s) from a sprain or other injury, or to facilitate the healing of an already injured ankle while protecting it from exacerbation. Heretofore, one of the most common way to support or brace the ankle was by "taping" it. In particular, some type of tape, e.g., adhesive, elastic, etc., was wound around the ankle and the foot to restrict transverse movement of the ankle while at the same time allowing for normal rotation of the ankle. However, the use of tape is time consuming and tedious and, depending upon the type of tape employed, may not be reusable. Therefore, reusable ankle braces and stabilizers have been developed which provide support for the ankle and can be applied and removed relatively easily.

Examples of such braces and stabilizers are found in the patent literature. For example, U.S. Pat. No. 3,506,000 (Baker) discloses a long and a short elastic strap connected to a rear portion which extends along the Achilles tendon and the back of the foot. The short elastic strap is connected at the medial or inner side of the foot while the longer elastic strap is crossed from the lateral or outer side of the foot to the medial side of the foot and attaches to the end of the shorter strap. A third non-elastic strap is connected to the rear portion of the ankle support and is wrapped around the foot.

U.S. Pat. No. 4,313,433 (Cramer) discloses an ankle stabilizer in the form of a flexible jacket which worn on the foot and extending over the top of the ankle. The jacket is elastic and includes laces to hold it in place and a pair of straps which are arranged to be wrapped around the jacket. In particular, one strap wraps over the instep, around the rear of the foot and ends on the medial side. The other strap wraps over the instep from the opposite direction, around the rear of the foot and ends on the lateral side. The free ends of the straps are secured in place by VELCRO® fasteners.

U.S. Pat. No. 4,323,058 (Detty) discloses an ankle brace in the form of a jacket to be worn on the foot and over the ankle. The jacket has a lateral side portion on which a pair of arcuate members are pivotally secured for conformance about the underlying malleolus. The jacket is arranged to be laced about the ankle by a first lace, with the arcuate members being laced together by a second lace to enable the arcuate members to closely conform and surround each malleolus. An elastic material lift strap is secured to the lateral side of the jacket and arranged to be wrapped thereabout in a figure-8 pattern to provide an upward lifting force to the jacket.

U.S. Pat. No. 4,597,395 (Barlow et al.) discloses an ankle support having an L-shape body into which the foot is placed. It includes a strap attached to the back of the L-shaped body with a VELCRO® fastener at each end. After the foot is placed within the body, each side of the strap is criss-crossed in turn from the back of the support to a position over the arch of the foot of the user.

U.S. Pat. No. 4,729,370 (Kallassy) discloses an ankle support in the form of a neoprene underliner or jacket which worn on the foot and extending over the top of the ankle. A non-stretch lateral strap is secured to the underliner at a point below the ankle joint on the lateral side of the foot. A non-stretch medial strap is then inelastically connected to the lateral strap.

Other U.S. Pat. Nos. disclosing various types of ankle braces are the following: 3,970,083 (Carrigan); 4,587,962 (Greene et al.); 4,624,244 (Taheri); 4,727,863 (Nelson).

While the aforementioned prior art ankle braces may be generally suitable for their intended purposes, they nevertheless leave something to be desired from the standpoints of accommodating various sized ankles, and also supplying sufficient customized support to the ankle. Thus, a need presently exists for an ankle brace which is of the one-size-fits-all type, which is simple in construction, easy to use, and which has means to adjust and customize the support applied by the brace, irrespective of the size of the ankle on which the brace is applied.

OBJECTS OF THE INVENTION

Accordingly, it is the general object of the instant invention to provide an ankle brace which improves upon, and overcomes the shortcomings of the prior art.

It is a further object of the instant invention to provide an ankle brace which can be applied to a wide range of sizes of ankles.

It is a further object of the instant invention to provide a one-size-fits-all ankle brace which can be readily applied to and removed from the ankle.

It is a further object of the instant invention to provide an ankle brace which is easy and inexpensive to manufacture.

It is yet a further object of the instant invention to provide an ankle brace wherein the amount of pressure exerted by the brace in preventing lateral or twisting movement of the ankle is adjustable.

It is an additional object of the instant invention to provide an ankle brace which provides good cushioning for the ankle to protect the ankle from impact injury.

It is yet an additional object of the instant invention to provide an ankle brace which provides thermal insulation at the ankle to maintain an elevated temperature thereat.

SUMMARY OF THE INVENTION

These and other objects of the instant invention are achieved by providing a brace for disposition on the ankle of a person. The brace comprises a base member and tension applying means. The base member is formed of an elastomeric material, e.g., neoprene having a tufted or plush fabric on its outer surface, having a pair of upper mounting straps and a pair of lower mounting straps.

The upper mounting straps are arranged to be wrapped about the leg of the person immediately above the ankle, with a portion of the upper mounting straps overlying the ankle. One of the upper mounting straps being located on one side of the ankle overlying the upper mounting strap on the other side of the ankle and being releasably securable thereto, e.g., by VELCRO® fastening means, at various points thereon irrespective of the size of the person wearing the brace. The lower mounting straps are arranged to be wrapped about the foot of the person, with one of the lower mounting straps on the other side of the ankle overlying the lower mounting strap on the one side of the ankle and being releasably securable thereto, e.g., by VELCRO® fastening means, at various points thereon irrespective of the size of the person wearing the brace.

The tensioning means is secured over the base member and comprises a pair of stretchable tension straps formed of an elastomeric material, e.g., fabric-covered-neoprene, which are arranged to be releasably secured to said base member at various points thereon to adjust the tension applied by the brace to the ankle.

DESCRIPTION OF THE DRAWING

Other objects and many of the intended advantages of this invention will be readily appreciated when the same becomes better understood by reference to the following detailed description, when considered in connection with the accompanying drawing wherein:

FIG. 2 is an enlarged sectional view of the ankle brace taken along the line 2—2 of FIG. 1;

DETAILED DESCRIPTION OF THE PREFERRED EMBODIMENTS

Figure 1:
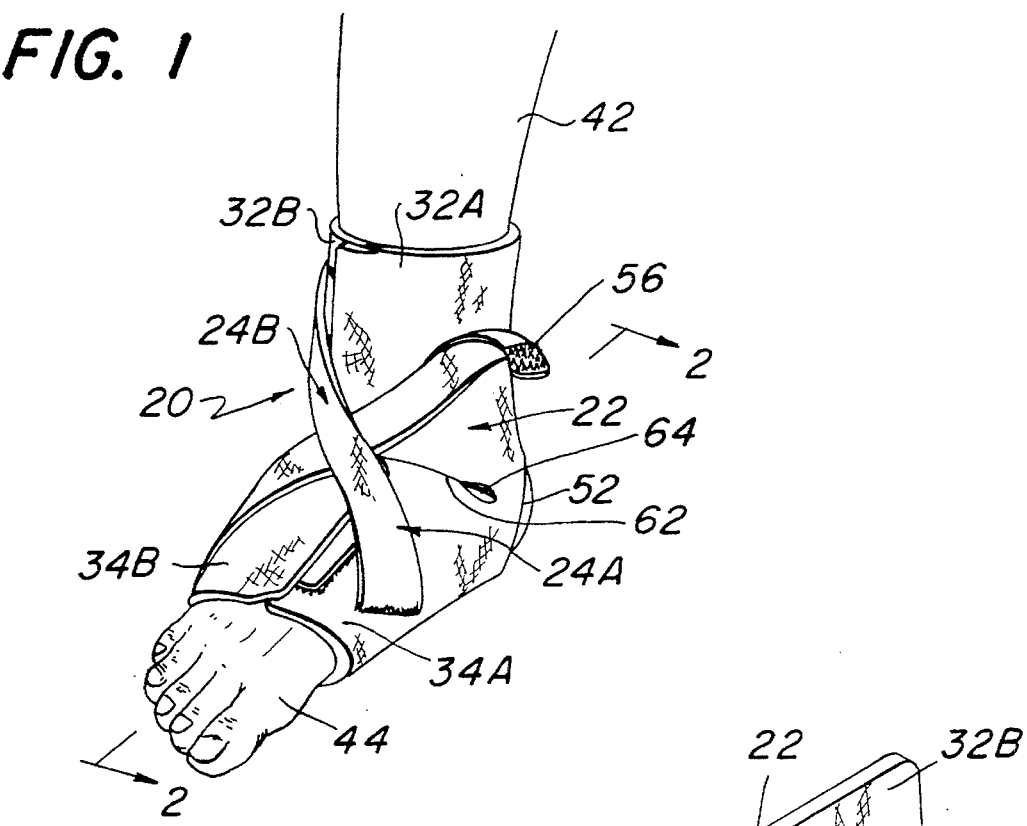
FIG. 1 is a perspective view of the ankle brace shown in place mounted on the leg and foot of the user so that it covers the user's ankle.

Referring now in greater detail to the various figures of the drawing, wherein like reference characters refer to like parts, there is shown in FIGS. 1–5 an ankle brace 20 constructed in accordance with the teachings of the present invention. The ankle brace 20 basically comprises a base member 22 and tension applying means in the form of a pair of tension straps 24A and 24B.

The base member can best be seen in FIG. 5 and basically comprises a unitary, planar sheet 26 of an elastomeric material cut into a predetermined shape, to be described later. The material is preferably a fabric-coated neoprene, with the fabric 28 being secured to the outer surface of the neoprene sheet. The neoprene is of a substantial thickness, e.g. approximately 4 mm. thick, to provide cushioning. In accordance with the preferred aspect of the invention, the fabric 28 is tufted or plush so that it can act as the multiple loop fastening component of a Velcro® fastening system. This feature facilitates the mounting of the brace on the knee of the wearer as will be described later.

Figure 5:
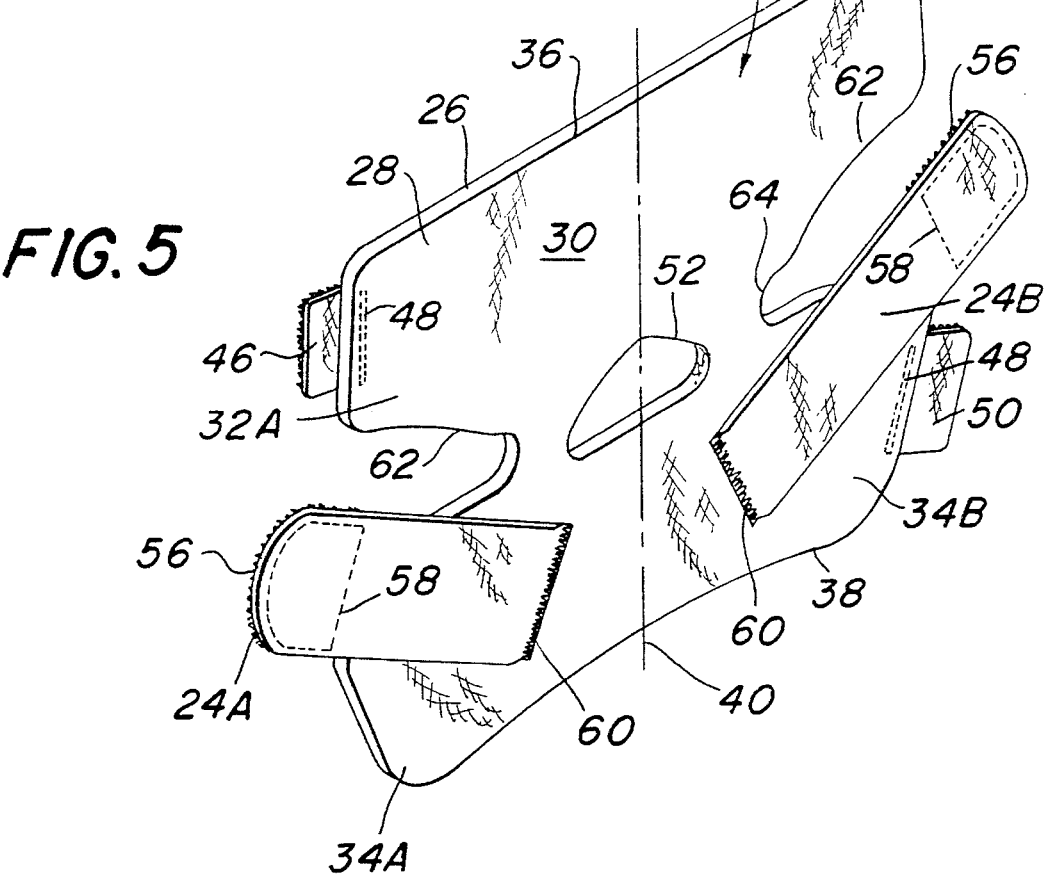
FIG. 5 is an enlarged perspective view of the ankle brace of FIG. 1 shown prior to application of the brace to the leg and foot of the user.

As can be seen clearly in FIG. 5 the base member 22 includes a central portion 30, a first upper mounting strap 32A, a second upper mounting strap 32B, a first lower mounting strap 34A, and a second lower mounting strap 34B. The straps project from respective portions of the central portion 30 of the base member. The central portion of the base member includes a linear upper edge 36, a somewhat arcuate (i.e., concave) lower edge 38, and a mid-line axis 40 extending through the central portion 30 of the base member through the upper and lower edges 36 and 38, respectively.

The upper straps 32A and 32B are each arranged to be bent or wrapped about a respective portion of the lower leg 42 (FIG. 1) of the wearer immediately above the ankle and over the ankle itself, so that the mid-portion 30 of the base member 22 is disposed over the achilles tendon area of the foot 44. Each of the lower mounting straps 34A and 34B is arranged to be bent or wrapped around the wearer's instep and arch immediately below the knee, all as shown in FIGS. 1 and 2.

The upper mounting strap 32A includes a tab 46 of a multi-hook Velcro® fastener secured to the inner surface of the free end thereof by plural stitches 48. The lower mounting strap 34B includes a similar hook Velcro® tab 50 secured to the inner surface of the free end thereof by plural stitches 48.

As can be seen, the Velcro® tab 46 of the upper mounting strap 32A extends in the opposite direction with respect to axis 40 to the Velcro® tab 50 of the lower mounting strap 34B. The reason for this tab arrangement is that the brace is designed so that the upper mounting strap 32A is to be wrapped around the leg over the upper mounting strap 32B so that the hooks of the tab 46 extend over the fabric surface 28 of the mounting strap 32B to enable the tab to be releasably secured to the multiple loops forming the plush fabric coating of the strap 32B. The amount of overlap is adjustable to accommodate any size of upper leg 42 so that the strap 32A and 32B encircle the leg to hold the brace in place thereon, and to adjust the amount of tension in the straps. The lower mounting strap 34B having the Velcro® tab 50 thereon is arranged to be wrapped about the lower limb 44 over the outer surface of the lower mounting strap 34A in a similar manner, albeit from the opposite direction. This mounts the lower portion of the base member on the foot, whereupon the base member is formed into a foot receiving jacket. Since the direction of wrapping the upper mounting straps and the lower mounting straps are in opposite directions the tension provided by the mounting of the brace on the ankle is equalized.

Figure 3:
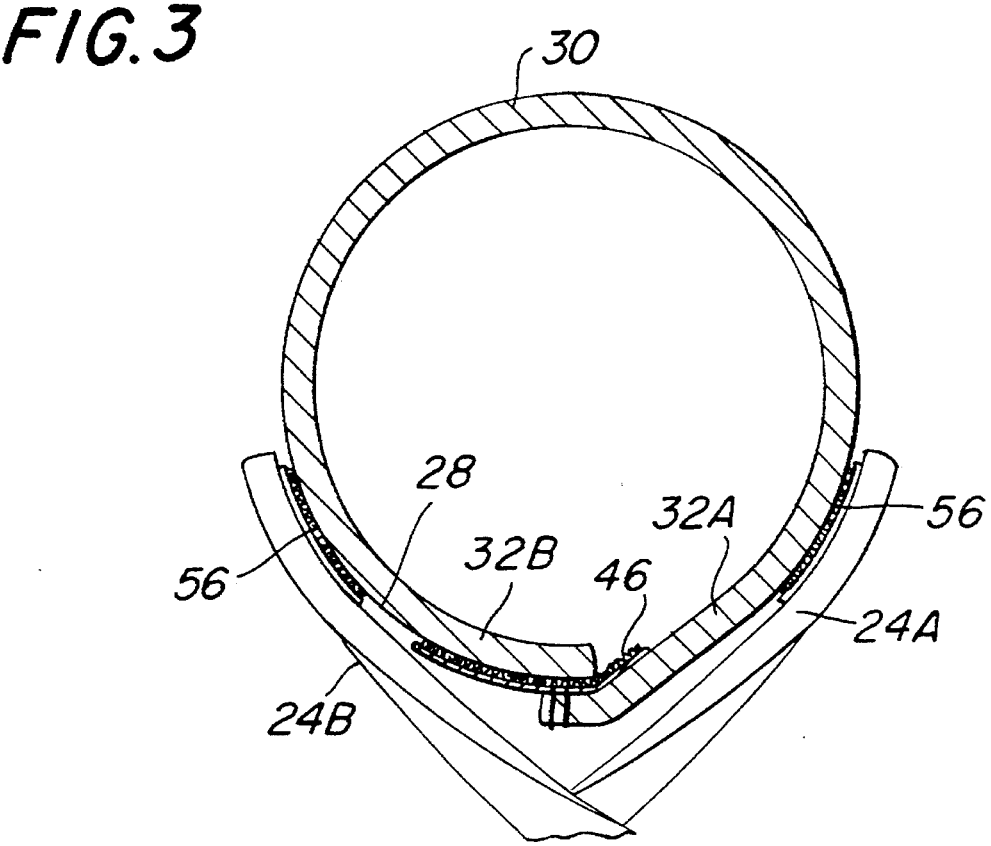
FIG. 3 is a sectional view of the ankle brace taken along the line 3—3 of FIG. 2.
Figure 4:
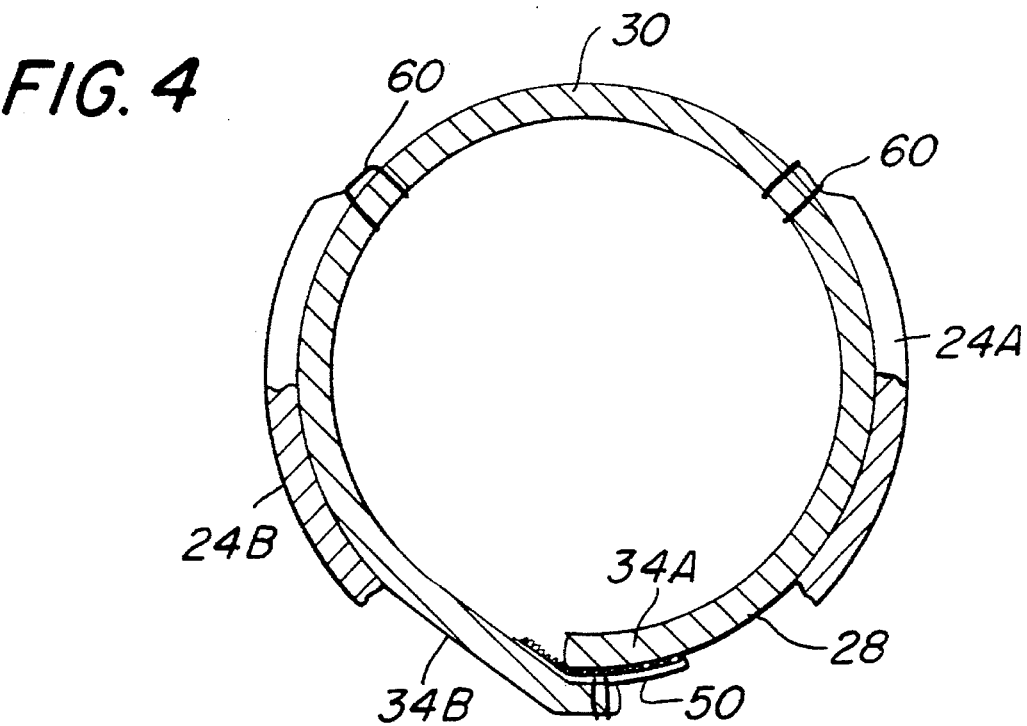
FIG. 4 is a sectional view of the ankle brace taken along the line 4—4 of FIG. 2.

As can be seen clearly in FIG. 3, the center of the central portion 30 of the base member 22 includes a generally triangular opening or a hole 52 therein. This hole is provided to accommodate the heel 54 of the foot 44, when the brace 20 is in place on the ankle as shown clearly in FIGS. 1 and 3.

The tension straps 24A and 24B are provided to enable the wearer to customize tension to be applied by the brace to the ankle at desired portions thereof. In accordance with the preferred embodiment of the invention, the tension straps are each elongated members of the same material, e.g., neoprene, and thickness as that of the base member 22. The free end of each of the tension straps 24A and 24B includes a respective multi-hook Velcro® patch 56 mounted on the inner surface thereof by stitches 58. The tension strap 24A is fixedly secured by stitches 60 to the lower portion of the base member at a point where the lower mounting strap 34A merges with the central portion 30 of the base member so that the strap extends upward and outward therefrom at an acute angle, e.g., approximately 45 degrees, to the axis 40. The other tension strap 24B is fixedly secured by stitches 60 to the lower portion of the base member at a point where the lower mounting strap 34B merges with the central portion 30 of the base member so that the strap extends upward and outward therefrom at the same acute angle, e.g., approximately 45 degrees, to the axis 40.

Referring now to FIGS. 1–4, the mounting of the brace on the ankle of a person will now be described. The brace is initially oriented like that shown in FIG. 5 so that it is generally planar. The brace is then laid down on some generally horizontal surface with its inner surface directed upward and the lower portion of the base member directed away from the wearer. The wearer then places his/her foot on the base member so that his/her arch is disposed on the middle portion 30 between the lower mounting straps 34A and 34B and his/her heel 54 is over the opening 52. The lower mounting strap 34A is then pulled or wrapped about the instep and held in place while the opposite lower mounting strap 34B having the Velcro® mounting tab 50 thereon is pulled and wrapped around the opposite portion of the instep. The tab 50 is then brought into engagement with the fabric 28 of the lower mounting strap 34A to thereby releasably secure the multiple hook-like elements of the tab to the fabric. This action overlaps the upper mounting strap 32A over the lower mounting strap 32B and releasably secures them together, with the amount of overlap being a function of the size of the wearer's foot and the degree of tension desired. Once this has been accomplished the lower portion of the brace is now mounted on the foot. Then the upper portion of the brace is folded upward so that the central portion 30 between the upper mounting straps 32A and 32B is held against the posterior portion of the wearer's lower leg 42 over the achilles tendon so that the wearer's heel 54 is fully received within the opening 52. The upper mounting strap 32B is then wrapped around the lower leg and ankle of the wearer to whatever degree of tension is desired. Then the opposite mounting strap 32B having the Velcro® attachment tab secured thereto is wrapped around the lower leg and ankle so that the tab is disposed over the outer fabric surface 28 of the mounting strap 32B. The amount of overlap and tension applied to the upper mounting strap is adjustable to whatever the wearer desires. Once the tab is disposed over the fabric covering on the opposite mounting strap, the multiple hook elements of the tab engage the plush fabric to releasably secure the upper mounting strap 32A over and to the upper mounting strap 32B. This action completes the mounting of the brace on the ankle.

Inasmuch as the material making up the base member is elastomeric, the mounting straps can stretch, thereby enabling the upper mounting straps to accommodate any size ankle, foot, and lower leg. Accordingly, a true, one-size-fits-all brace is provided. Moreover, the thickness of the neoprene material making up brace serves to protect the ankle from impact injury when the brace is worn. Further still, the thickness of the neoprene material of the brace coupled with its thermally insulative properties, insures that when the brace is worn, heat will be retained under the brace, thereby keeping the ankle at an elevated temperature. This elevated temperature can facilitate healing of an injury or prevent the exacerbation thereof.

Additional bracing or stabilization for the ankle is provided by the brace by stretching a selected one, and preferably both, of the tension straps 24A and 24B over respective portions of the mounting straps of the base member and securing those tension straps thereto. This can be readily accomplished since the outer surface 28 of the base member is entirely covered with the plush fabric, whereupon the Velcro® patches 56 of the tension straps can be releasably secured thereto when they engage that surface.

Even though the tension straps are normally oriented so that they naturally extend at a predetermined acute angle to the axis 40 of the brace, each of the tension straps can be extended or stretched to various positions and locations on the upper mounting straps so long as it is within the range of movement of the tension strap. Thus, the tension strap 24A can be stretched across the instep so that its free end is disposed over the upper mounting strap 32B and secured thereto at any point thereon by the Velcro® patch 56. In a similar manner the tension strap 24B can be stretched across the instep so that its free end is disposed over the upper mounting strap 32A and secured thereto at any point thereon by the Velcro® patch 56.

With the crossing of the tension straps additional stabilization, e.g., resistance to twisting, of the ankle results over that which is provided by the base member itself. Moreover, the amount of tension and the direction it is applied by the ability of the tension straps to be secured to the mounting straps at various positions, enables user to customize the support and stabilization provided by the brace to his/her desires or needs, irrespective of the size of the ankle.

As can be seen clearly in FIG. 5 a generally V-shaped recess 62 exists between the upper mounting strap 32A and the lower mounting strap 34A. The apex of the recess is somewhat circular. A similar V-shaped recess 62 exists between the upper mounting strap 32B and the lower mounting strap 34B. Accordingly, when the brace 20 of the subject invention is mounted on the ankle the marginal edges two V-shaped recesses 74 squeeze together, as shown clearly in FIG. 1, to thereby prevent bunching up of the material making up the brace. This ensures that the brace can be worn comfortably.

It should be pointed out at this junction that other materials, than those described heretofore, can be used to make the ankle brace of this invention. For example, neoprene having a tufted fabric covering may not be used, i.e., the neoprene may not be covered by any fabric or may be covered by a non-tufted fabric, such as smooth nylon. In the case where the material of the base member does not include a plush fabric covering, the outer surface of the base member should include at least patches of a plush or multi-loop VELCRO® component fixedly secured thereto for engagement by the multi-hook VELCRO® component of the tabs of the mounting straps and the patches of the tension straps to enable those straps to be secured thereto at various positions thereon. In fact, other releasably securable means can be used in lieu of VELCRO® components, if desired. Moreover, in some cases, it may not be desired to use neoprene as the material of the base member and/or the tension straps. Thus, other elastic materials, with or without cushioning and thermal retention properties may be used, for either the base member or the tension straps. Further still, the base member and the tension straps need not be unitary members, i.e., each formed of a single piece of material. Thus, the base member may be formed of plural pieces which are secured together to form an integral assembly. Each tension strap may also be an assembly, if desired.

As should be appreciated by those skilled in the art, not only is the subject brace a true one-size-fits-all device which can be readily applied and adjusted to provide customized stabilization and support, its construction is very simple. In this regard it can be readily fabricated from a sheet of fabric-covered-neoprene or some other elastomeric material. Once fabricated and assembled, its generally flat shape enables it to be transported and warehoused inexpensively, as compared to the prior art.

Without further elaboration, the foregoing will so fully illustrate my invention that others may, by applying current or future knowledge, readily adapt the same for use under the various conditions of service.

I claim:

1. A brace for disposition on the ankle of a person, said brace comprising a generally planar base member and generally planar tension applying means secured thereto, said base member and said tension applying means being arranged to be laid flat to facilitate the mounting of the brace on the ankle by wrapping portions thereof about the foot, said base member being formed of an elastomeric material having a central portion having a longitudinal axis from which a pair of upper mounting straps and a pair of lower mounting straps extend, said upper mounting straps comprising a first upper mounting strap and a second upper mounting strap, said first upper mounting strap being arranged to be wrapped about the leg of the person immediately above the ankle from a first direction, said second upper mounting strap being arranged to be wrapped about the leg of the person immediately above the ankle from a second direction, opposite to said first direction, whereupon a portion of said first and second upper mounting straps overlie the ankle, with said first upper mounting strap overlying said second upper mounting strap and being releasably securable thereto at various points thereon irrespective of the size of the leg of the person, said lower mounting straps being arranged to be wrapped about the foot of the person from opposite directions, with said first lower mounting strap being arranged to be wrapped about the foot of the person from said first direction and wherein said second lower mounting strap is arranged to be wrapped about the foot of the person from said second direction and over said first lower mounting strap, whereupon said second lower mounting strap is releasably securable to said first lower mounting strap at various points thereon irrespective of the size of foot of the person, said tensioning means comprises plural stretchable tension straps secured to said base member on opposite sides of said axis, each of said tension straps comprising an elastomeric material having a free end, said tension straps being arranged to be crossed over each other and over said base member so that the free ends thereof are releasably secured to said base member at various selectable points thereon to adjust the tension applied by the brace to the ankle.

2. The ankle brace of claim 1 wherein said base member further comprises an opening for receiving the heel of the person when said brace is worn.

3. The ankle brace of claim 1 wherein said free end of one of said tension straps is arranged to be extended across the instep of the person for releasable securement to said upper mounting strap on the opposite side of the brace from the side to which said one tension strap is fixedly secured, and wherein said free end of the other of said tension straps is arranged to be extended across the instep of the person for releasable securement to said upper mounting strap on the opposite side of the brace from the side to which said other tension strap is fixedly secured.

4. The ankle brace of claim 1 wherein a pair of recesses are located between said upper mounting straps and said lower mounting straps to prevent bunching of the material forming the brace when the brace is in place on the ankle.

5. The ankle brace of claim 1 wherein said elastomeric material comprises neoprene.

6. The ankle brace of claim 1 wherein said releasable securement of said mounting straps together is by use of fastening means.

7. The ankle brace of claim 1 wherein said fastening means comprises a tab of a multi-hook component fixedly secured to the first upper mounting strap on the one side of the ankle, and a tab of a multi-hook component fixedly secured to the second lower mounting strap on the other side of the ankle, and wherein said base member comprises an outer surface, with the outer surface of the mounting straps of said base member forming a multi-loop component for releasable engagement by said multi-hook tabs.

8. The ankle brace of claim 1 wherein said releasable securement of said tensioning straps to said mounting straps is by use of fastening means.

9. The ankle brace of claim 8 wherein said fastening means comprises respective patches of a multi-hook component fixedly secured to respective ones of said tension straps, with the outer surface of the mounting straps of said base member forming a multi-loop component for releasable engagement by said multi-hook patches.

10. The ankle brace of claim 7 wherein said releasable securement of said tensioning straps to said mounting straps is by use of VELCRO® fastening means.

11. The ankle brace of claim 10 wherein said fastening means comprises respective patches of a multi-hook component fixedly secured to respective ones of said tension straps, with the outer surface of the mounting straps of said base member forming a multi-loop component for releasable engagement by said multi-hook patches.

12. The ankle brace of claim 11 wherein a pair of recesses are located between said upper mounting straps and said lower mounting straps to prevent bunching of the material forming the brace when the brace is in place on the ankle.

13. The ankle brace of claim 3 wherein a pair of recesses are located between said upper mounting straps and said lower mounting straps to prevent bunching of the material forming the brace when the brace is in place on the ankle.

14. The ankle brace of claim 13 wherein said elastomeric material comprises neoprene.

15. The ankle brace of claim 13 wherein said releasable securement of said mounting straps together is by use of fastening means.

16. The ankle brace of claim 15 wherein said fastening means comprises a tab of a multi-hook component fixedly secured to the first upper mounting strap on the one side of the ankle, and a tab of a multi-hook component fixedly secured to the second lower mounting strap on the other side of the ankle, and wherein said base member comprises an outer surface, with the outer surface of the mounting straps of said base member forming a multi-loop component for releasable engagement by said multi-hook tabs.

17. The ankle brace of claim 16 wherein said free end of one of said tension straps is arranged to be extended across the instep of the person for releasable securement to said upper mounting strap on the opposite side of the brace from the side to which said one tension strap is fixedly secured, and wherein said free end of the other of said tension straps is arranged to be extended across the instep of the person for releasable securement to said upper mounting strap on the opposite side of the brace from the side to which said other tension strap is fixedly secured.

18. The ankle brace of claim 17 wherein said releasable securement of said tensioning straps to said mounting straps is by use of fastening means.

19. The ankle brace of claim 18 wherein said fastening means comprises respective patches of a multi-hook component fixedly secured to respective ones of said tension straps, with the outer surface of the mounting straps of said base member forming a multi-loop component for releasable engagement by said multi-hook patches.

* * * * *